US012636430B2

(12) United States Patent
Dimaio et al.

(10) Patent No.: US 12,636,430 B2
(45) Date of Patent: May 26, 2026

(54) SPACE-EFFICIENT FREE PISTON RESERVOIR FOR A WEARABLE DRUG DELIVERY DEVICE

(71) Applicant: Insulet Corporation, Acton, MA (US)

(72) Inventors: Cameron Dimaio, Linwood, NJ (US); Steven Cardinali, Tewksbury, MA (US)

(73) Assignee: INSULET CORPORATION, Acton, MA (US)

( * ) Notice: Subject to any disclaimer, the term of this patent is extended or adjusted under 35 U.S.C. 154(b) by 785 days.

(21) Appl. No.: 17/812,064

(22) Filed: Jul. 12, 2022

(65) Prior Publication Data

US 2023/0014094 A1 Jan. 19, 2023

Related U.S. Application Data

(60) Provisional application No. 63/222,495, filed on Jul. 16, 2021.

(51) Int. Cl.
*A61M 5/145* (2006.01)
*A61M 5/14* (2006.01)
(Continued)

(52) U.S. Cl.
CPC ...... *A61M 5/14526* (2013.01); *A61M 5/1408* (2013.01); *A61M 5/14244* (2013.01); *A61M 5/158* (2013.01)

(58) Field of Classification Search
CPC ............ A61M 5/14526; A61M 5/1407; A61M 5/1408; A61M 5/1409; A61M 5/19; A61M 2209/045; A61J 1/20; F04B 7/0053
See application file for complete search history.

(56) References Cited

U.S. PATENT DOCUMENTS

| | | | | | |
|---|---|---|---|---|---|
| 4,610,666 | A | * | 9/1986 | Pizzino | A61M 5/19 |
| | | | | | 604/249 |
| 4,795,441 | A | * | 1/1989 | Bhatt | A61G 7/0503 |
| | | | | | 604/7 |

(Continued)

FOREIGN PATENT DOCUMENTS

| | | |
|---|---|---|
| CN | 107096091 A | 8/2017 |
| EP | 0789146 A1 | 8/1997 |

(Continued)

OTHER PUBLICATIONS

International Search Report and Written Opinion, Application No. PCT/US2022/016713, mailed Aug. 5, 2022, 19 pages.

(Continued)

*Primary Examiner* — Laura A Bouchelle
(74) *Attorney, Agent, or Firm* — Goodwin Procter LLP

(57) ABSTRACT

Disclosed herein is a reservoir for use in a wearable drug delivery device having multiple chambers of potentially varying lengths or arrangement so as to efficiently utilize available space within a housing of the drug delivery device. Each of the chambers is connected to a fluid path and a liquid drug is drawn from each of the chambers by suction applied to the fluid path. Each of the chambers is fitted with a free piston which is moved within the chamber by the suction applied to the fluid path as it draws the liquid drug out of the chamber, thereby eliminating the need for a mechanical arrangement for moving the piston within each of the chambers.

17 Claims, 9 Drawing Sheets

(51) Int. Cl.
    *A61M 5/142*         (2006.01)
    *A61M 5/158*         (2006.01)

(56)         References Cited

U.S. PATENT DOCUMENTS

| | | | |
|---|---|---|---|
| 4,991,743 A | | 2/1991 | Walker |
| 5,368,570 A | | 11/1994 | Thompson et al. |
| 5,906,592 A | | 5/1999 | Kriesel et al. |
| 6,740,059 B2 | | 5/2004 | Flaherty |
| 7,137,964 B2 | | 11/2006 | Flaherty |
| 7,278,985 B2 | * | 10/2007 | .ANG.gerup ..... A61M 5/14216 |
| | | | 604/181 |
| 7,303,549 B2 | | 12/2007 | Flaherty |
| 7,488,307 B2 | * | 2/2009 | Rimlinger ........... A61M 5/3202 |
| | | | 604/110 |
| 8,734,396 B2 | | 5/2014 | Wyss |
| 9,981,082 B2 | * | 5/2018 | Fish .................. A61M 5/16881 |
| 11,944,588 B2 | * | 4/2024 | McLoughlin ............. A61J 1/20 |
| 2003/0198558 A1 | | 10/2003 | Nason et al. |
| 2004/0115068 A1 | | 6/2004 | Hansen et al. |
| 2007/0255260 A1 | | 11/2007 | Haase |
| 2011/0108158 A1 | | 5/2011 | Huwiler et al. |
| 2011/0319814 A1 | | 12/2011 | Sullivan et al. |
| 2017/0290975 A1 | | 10/2017 | Barmaimon et al. |

FOREIGN PATENT DOCUMENTS

| | | | | |
|---|---|---|---|---|
| EP | 1065378 | A2 | 1/2001 | |
| EP | 2229970 | A1 | 9/2010 | |
| EP | 2556815 | A1 | 2/2013 | |
| WO | WO-9415664 | A1 * | 7/1994 | ........... A61M 39/02 |
| WO | 2012065780 | A2 | 5/2012 | |
| WO | 2013149186 | A1 | 10/2013 | |

OTHER PUBLICATIONS

European Search Report and Written Opinion, Application No. EP02768908, dated Apr. 30, 2010.
International Search Report and Written Opinion, Application No. PCT/US2019/042233, mailed Jan. 3, 2020, 14 pages.
International Search Report and Written Opinion, Application No. PCT/US2021/060148, mailed Mar. 17, 2022, 17 pages.

* cited by examiner

100

SPACE-EFFICIENT FREE PISTON RESERVOIR FOR A WEARABLE DRUG DELIVERY DEVICE

RELATED APPLICATIONS

This application claims the benefit of U.S. Provisional Patent Application No. 63/222,495, filed Jul. 16, 2021, the contents of which are incorporated herein by reference in their entirety.

BACKGROUND

Many conventional drug delivery systems, including, for example, wearable drug delivery devices, include a drug container, often referred to as a reservoir, that stores a liquid drug for delivery to a user in accordance with an algorithm. A liquid drug stored in the reservoir may be delivered to the user by expelling the drug from the reservoir using a driven plunger, for example, a plunger driven by a leadscrew. An example of a typical wearable drug delivery device is shown in FIG. 1 as reference number 100. In such wearable, on-body devices, it is desirable to keep the overall drug delivery device 100 as small as possible to minimize the impact to the wearer and to provide a sleek, curved design to eliminate exterior corners.

One limitation of the current design of the reservoir, in which the plunger is driven with a leadscrew, is that the total footprint of the reservoir and drive mechanism must be greater than the length of reservoir, often by as much as 2 times. This is due to the fact that the leadscrew needs to extend all of the way into the reservoir when the reservoir is in the empty state (i.e., it must be approximately equal to the length of the reservoir minus space taken by plunger). When the reservoir is full, however, the leadscrew will necessarily extend behind the reservoir to occupy a space of a length up to the length of the reservoir.

Another limitation of typical prior art designs of the reservoir is that, in a wearable drug delivery device having a sleek, curved design, as in FIG. 1, there may be wasted interior space due to the fact that the reservoir comprises a single, unitary (and often cylindrical) structure for containing the liquid drug, and thus may be required to be disposed in areas of the device having a large longitudinal length. As such, interior areas near the curved surfaces of the housing, wherein the overall longitudinal length of the housing is smaller, may be wasted.

Therefore, it would be desirable to replace the prior art reservoir with a design that eliminates the leadscrew to minimize the overall length of the reservoir and which fits into the otherwise empty wasted spaces within the interior of the housing of the wearable drug delivery device.

SUMMARY OF THE INVENTION

The embodiments of the invention described herein address the problems identified above. Each embodiment eliminates the leadscrew by having free pistons which are moved within the reservoir chambers by suction applied to the fluid port. In addition, the embodiments herein have replaced the single large reservoir chamber of prior art embodiments with multiple chambers which may have any convenient length and/or configuration designed to make more efficient use of the space within the housing of the wearable drug delivery device.

BRIEF DESCRIPTION OF THE DRAWINGS

FIG. 3(*b*) is a ghosted view of a wearable drug delivery device showing the embodiment of FIGS. 2(*a,b*) in situ in the device.

FIG. 7(*b*) is an end view of the second embodiment of FIG. 6 showing the fluid ports.

DETAILED DESCRIPTION

The novel aspects of the embodiments of the present invention, which are described in detail below, are, inter alia, the free pistons which eliminate the need for the leadscrew and the multi-chamber reservoir which can be sized and configured to efficiently utilize space within the housing of the wearable drug delivery device. In all embodiments of the invention, the liquid drug stored in the multiple chambers is drawn into a fluid port with suction which in turn moves the free pistons within the chambers. Several exemplary embodiments are shown herein; however, it should be realized that the invention is not meant to be limited thereby but is instead meant to encompass the novel aspects of the various embodiments.

Figure 1:
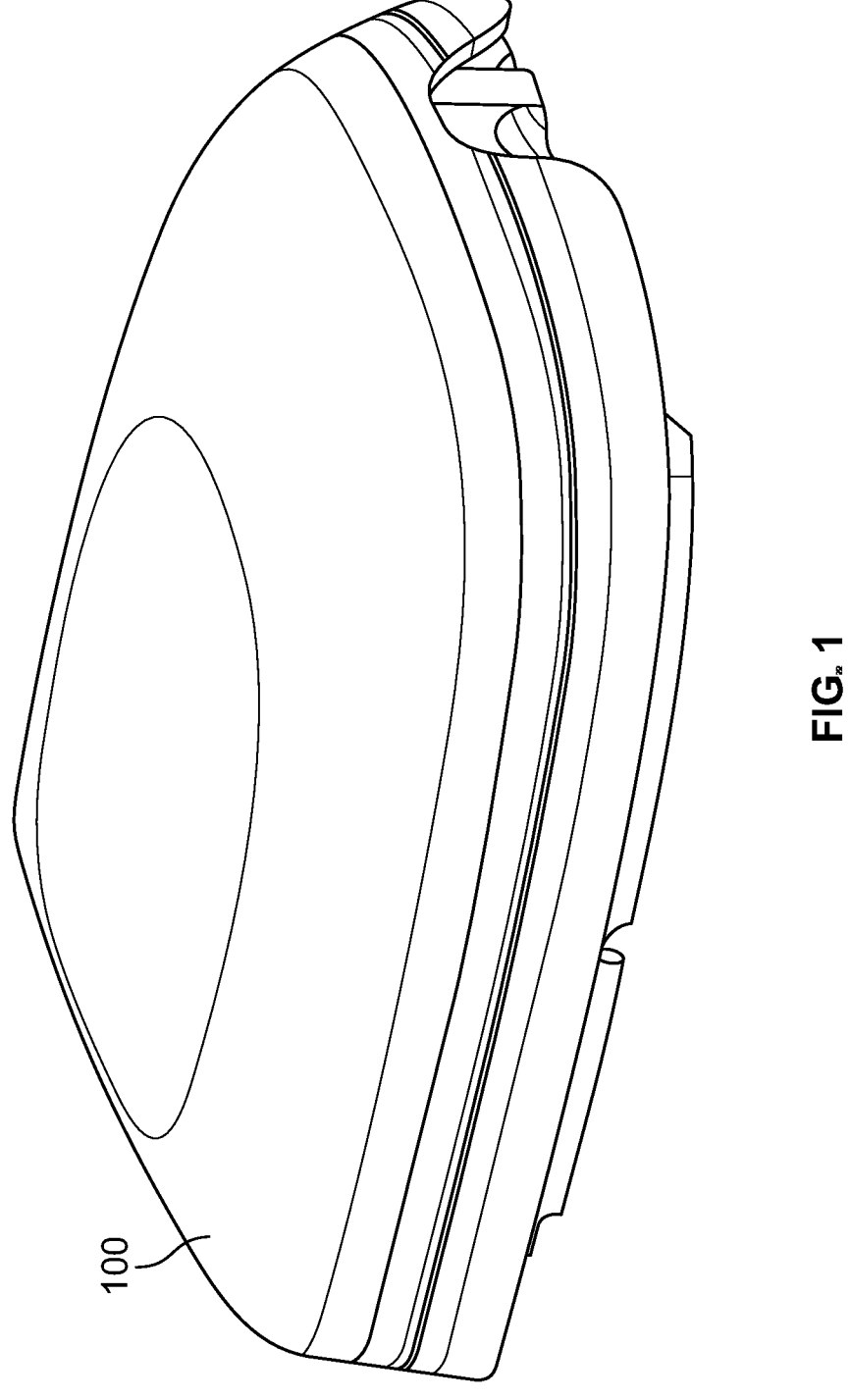
FIG. 1 is a prior art wearable drug delivery device.
Figure 2A:
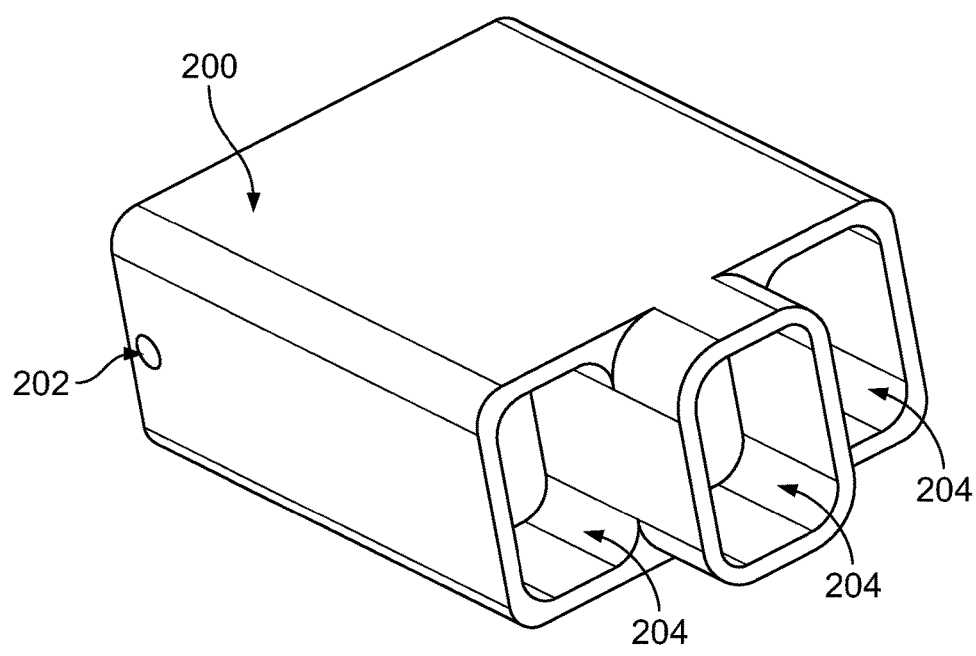
FIG. 2(*a,b*) is a perspective view and a cross-sectional view of a first embodiment of the invention, respectively showing a multi-chamber reservoir with three pistons.
Figure 2B:
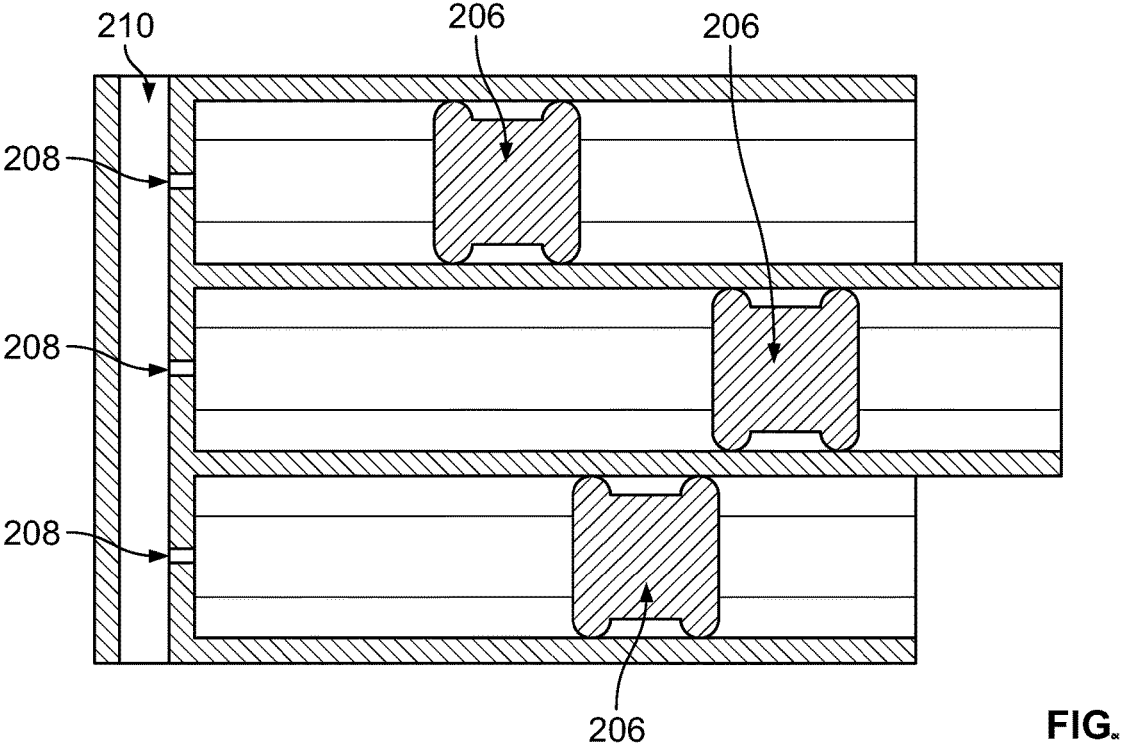

FIGS. 2(*a,b*) show perspective and cross-sectional views of a first embodiment of the invention respectively. In this embodiment, the device comprises three separate chambers 204 in a side-by-side configuration. The different lengths of chambers 204 serve to more efficiently utilize space within the curvature of the housing of the wearable drug delivery device 100. Disposed within each chamber 204 is a free piston 206. As used herein, the term "free piston" is meant to refer to a piston that is not driven by mechanical means, for example, a leadscrew.

In embodiments of the invention, the free pistons 206 may be of any shape to match the cross-sectional shape of the chamber 204 in which they are deployed. In exemplary embodiments free piston 206 may be spherical or cuboidal in shape. In certain embodiments, free pistons 206 may be configured with one or more O-rings along a circumferential surface thereof to provide a fluid seal between free piston 206 and chamber 204. Free pistons 206 may have a planar surface that abuts against a planar surface of chamber 204, or a rounded surface that abuts against a concave end surface of chamber 204.

The device may be configured with a fluid path 210 which is in fluid communication with each of chambers 204 via fluid connections 208. Fluid path 210 may be closed on one end thereof and connected to a fill/dispense port 202 on the opposite end thereof. In one aspect of the invention, the multiple chambers 204 may be molded into a unitary body 200. In other aspects of the invention, multiple chambers 204 may be molded separately and connected to fluid path 210.

In operation, chambers 204 may be filled by forcing the liquid drug into fill/dispense port 202 under pressure. In one embodiment, the liquid drug may be, for example, forced into fill/dispense port 202 using a hypodermic needle inserted into fill/dispense port 202 or an adjacent port. In other embodiments, fill/dispense port 202 may be connected to an interface which allows both filling and extraction of the liquid drug 204. The liquid drug, upon entering fluid path 210 under pressure will flow into chambers 204 via openings or connections 208 and will force pistons 206 toward the open end of chambers 204 (on the righthand side of FIGS. 2a, 2b). The open end of chambers 204 may have an end cap, as explained in other embodiments, but such end caps are not shown here for purposes of clarity. To draw the liquid drug out of chambers 204, suction is applied to fill/dispense port 202 causing the liquid drug in chambers 204 to be drawn into fluid path 210 via connections 208 and ultimately out of the reservoir through fill/dispense port 202. The suction which causes the liquid drug to migrate from the fluid chambers 204 to fill/dispense port 202 also serves to pull pistons 206 toward fluid path 210.

In various embodiments of the invention, the suction required to migrate the liquid drug from the fluid chambers 204 to fill/dispense port 202 and to pull free pistons 206 toward fluid path 210 may be provided by, for example, a reciprocating pump (not shown) that alternates between pulling (i.e., creating a suction force on the reservoir) and pushing (i.e., creating a pressure to force the liquid drug into the patient). In other embodiments, any means of creating the required suction or pressure may be used.

Figure 3B:
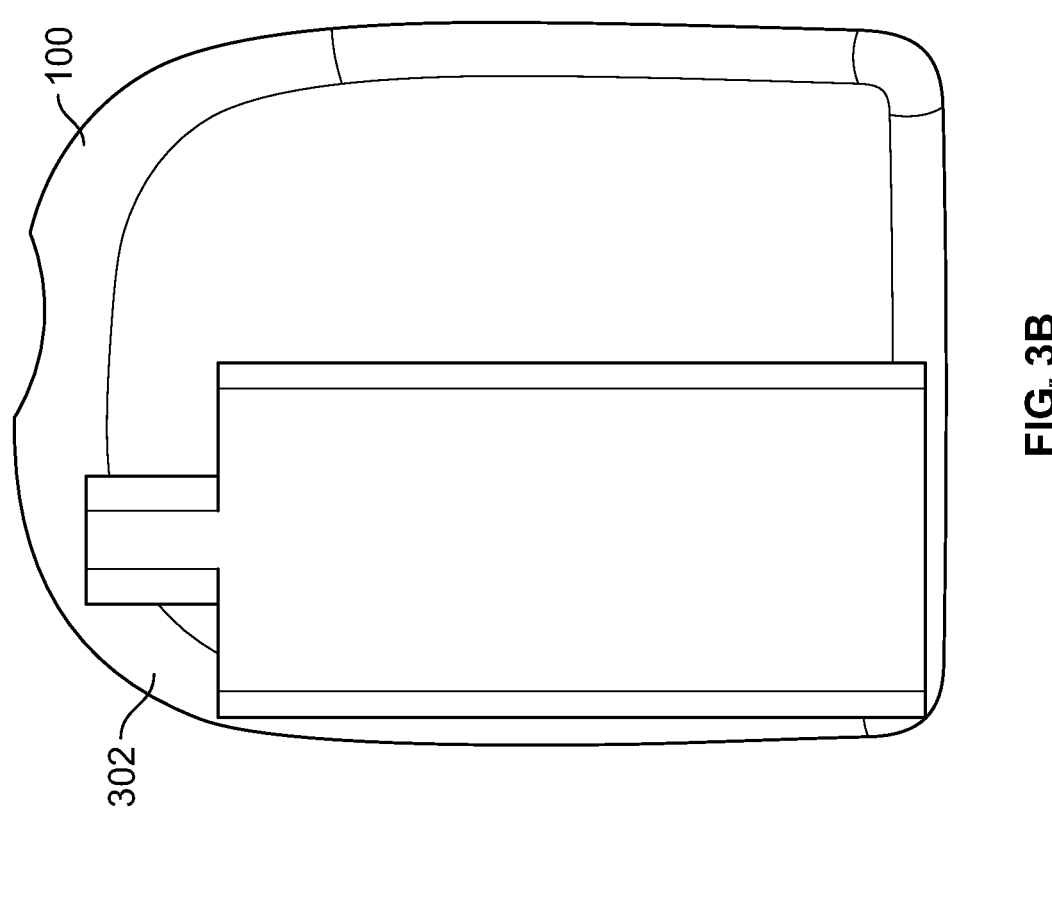
FIG. 3(*a*) is a ghosted view of a prior art wearable drug delivery device showing the positioning of the single-chamber prior art reservoir therein.
Figure 3A:
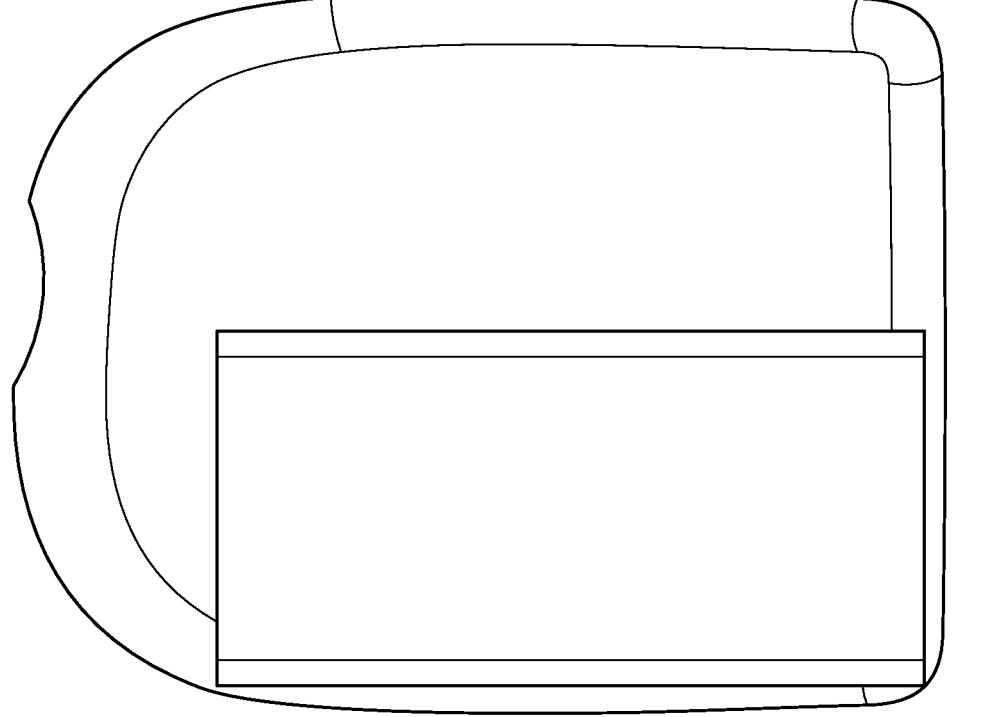

FIG. 3 shows an in situ comparison of the prior art, single-chamber reservoir in view (a) versus the multi-chamber reservoir of the present invention in view (b). It should be noted that the reservoir of the present invention makes more efficient use of the space within the housing of drug delivery device 100. As can be seen in view (a), the single-chamber prior art reservoir is limited in its length by the curvature of the housing whereas the multi-chambered reservoir of the present invention is able to take advantage of the area near the curvature of the housing. Furthermore, the reservoir may have an extended length, thereby allowing it to hold more liquid drug, because of the elimination of the need for the leadscrew to drive the pistons within the chambers. As may be realized, the space within the housing of drug delivery device 100 may be utilized even more efficiently in variations of embodiments in accordance with the present invention having more than three chambers, for example, multiple smaller chambers of varying lengths which may be able to utilize, for example, area 302 in view (b).

Figure 4:
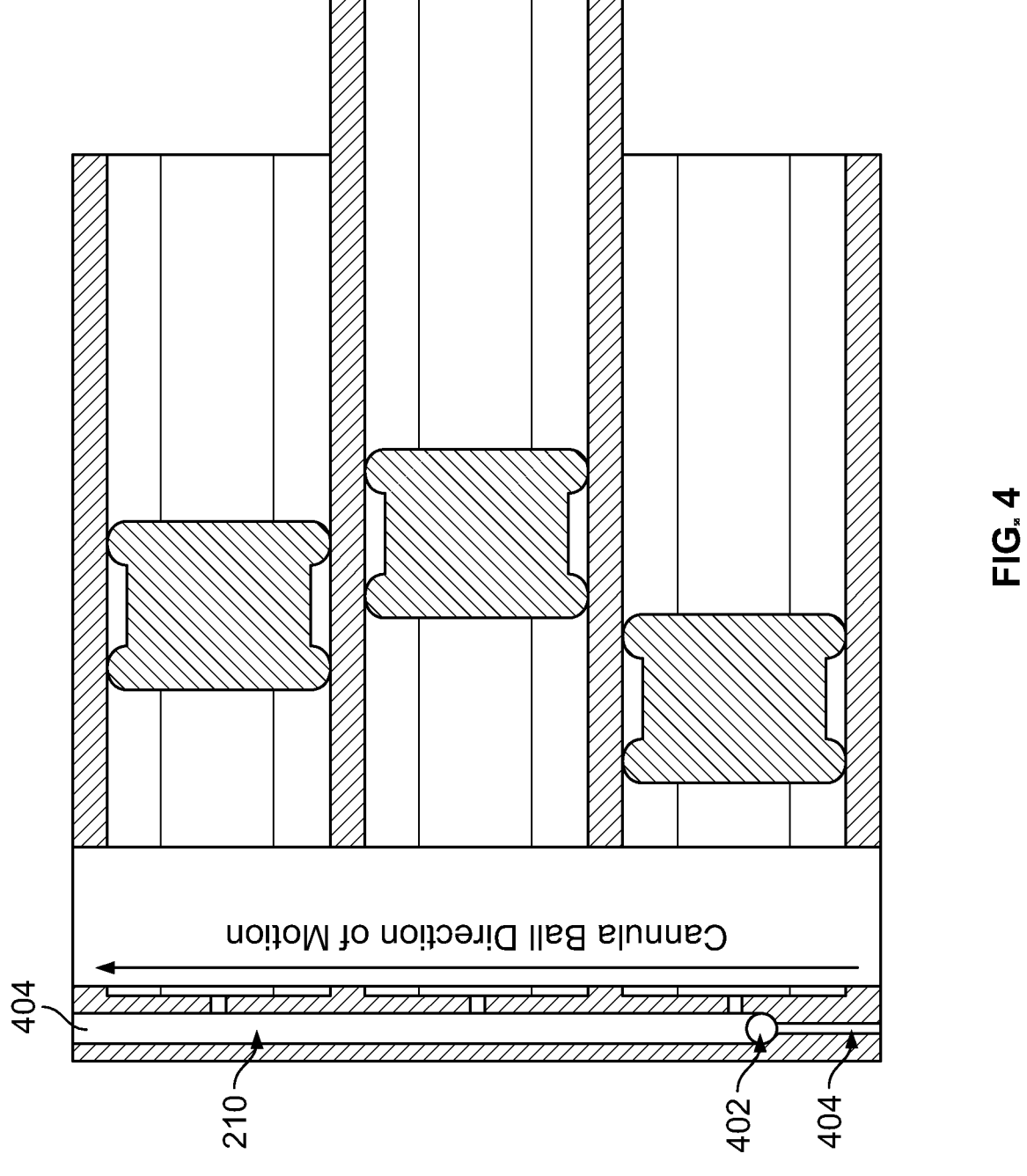
FIG. 4 is a cross-sectional view of a first variation of the embodiment of FIGS. 2(*a,b*).

FIG. 4 shows a variation of the embodiments of FIG. 2 in which a spherical piston or cannula ball 402 is disposed within fluid path 210 to clear any remaining hold-up volume of liquid drug in fluid path 210 after chambers 204 have emptied, such as to avoid wasting the liquid drug remaining in fluid path 210. After chambers 204 have emptied, cannula ball 402 will be drawn by suction along fluid path 210 toward position 404, thereby forcing any liquid drug remaining in fluid path 210 out of the reservoir via fill/dispense port 202. In certain embodiments, the cannula ball may be held in its initial position until the chambers 204 have been emptied by providing the cannula ball 402 with a stronger resistive or frictional force than the pistons 206 by making the seal of cannula ball 402 within fluid path 210 tighter than the seals of pistons 206 within chambers 204. As such, the path of least resistance will be drawing liquid drug from chambers 204 and moving pistons 206 toward fluid path 210 until chambers 204 are empty. Cannula ball 402 will thereby only be able to move once the chambers 204 have been emptied. An air inlet 404 may be provided to allow the motion of the cannula ball 402. The air inlet 404 may have a reduced diameter relative to fluid path 210 to prevent over travel or escape of the cannula ball 402.

In preferred implementations of the embodiments heretofore discussed, the resistive force on each of pistons 206 should be relatively equal such that the liquid drug is drawn equally from each of chambers 204. However, variations in the resistance of each piston 206, as well as the relative differences in length of the chambers 204 may cause some chambers to empty before others. However, continued suction at fill/dispense port 202 will simply cause the other chambers 204 to become empty at different times. As such, in some embodiments, chambers 204 may dispense drug at substantially the same time, and in other embodiments, chambers 204 may dispense drug sequentially, at different times.

Figure 5:
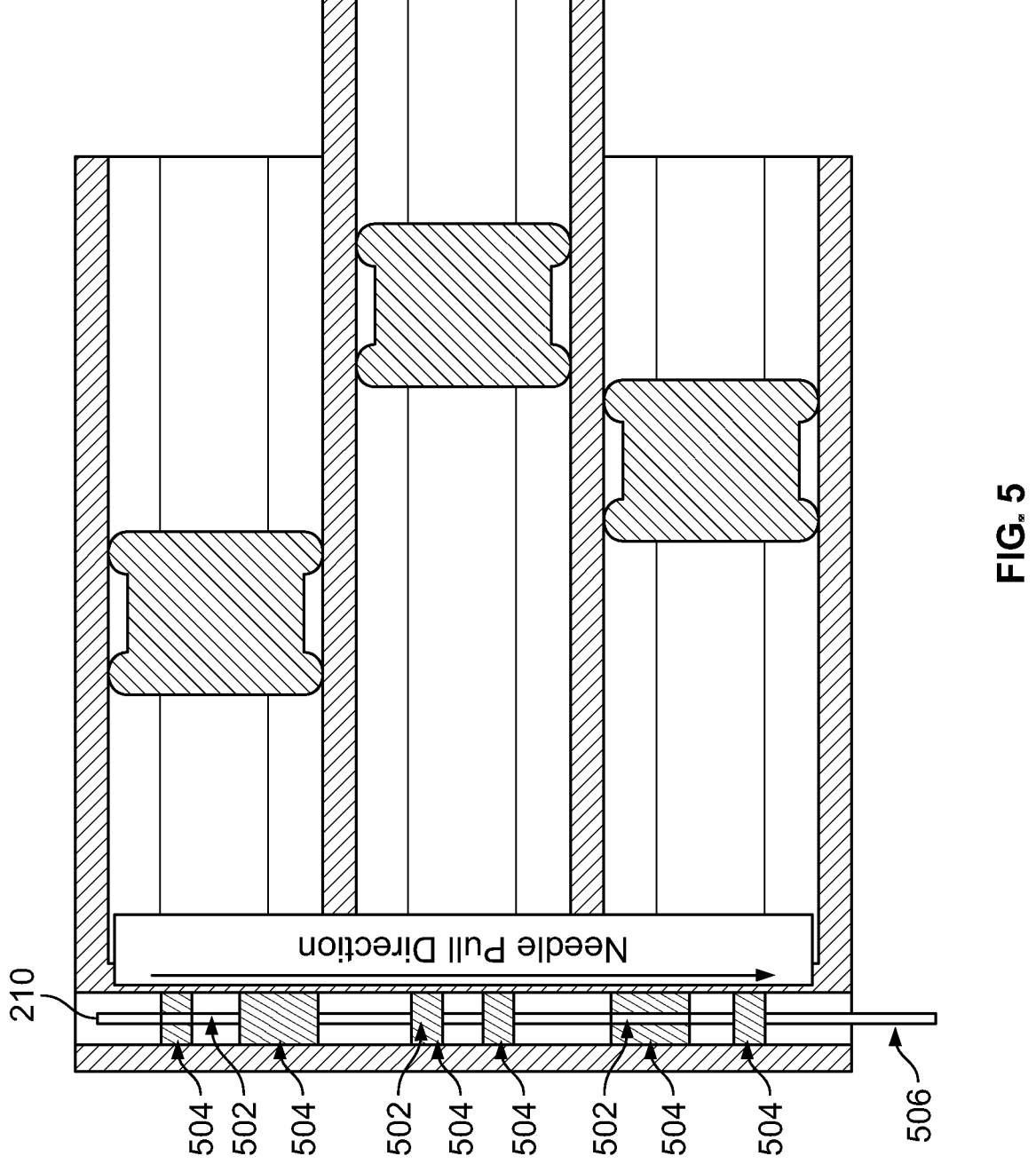
FIG. 5 is a cross-sectional view of the second variation of the embodiment of FIGS. 2(*a,b*).

FIG. 5 shows an embodiment of the invention in which the liquid drug may be drawn from each of chambers 204 on an individual basis. This may provide advantages, for example, in cases where individual chambers 204 are filled with different liquid drugs. For example, one or more of chambers 204 may contain insulin of a particular concentration, while others of chambers 204 may contain GLP-1 or insulin of a different concentration. The ability to access individual chambers 204 may be accomplished by way of pulling or pushing a side-slit needle 506 through various septa 504 disposed within fluid path 210. As an example, in embodiments wherein the reservoir is provided with three chambers 204, such as the embodiment shown in FIG. 2, the needle 506 will be provided with three side-slit holes 502 and will be plugged on one end. The side-slit holes 502 are spaced such that the needle 506 can be pulled or pushed a repeated discrete distance to open the fluid path to individual reservoir chambers 204. Septa 504 are placed around the openings to the chambers 204 to seal the chambers 204 from one another and to seal the inactive side-slit holes 502 on the needle 506. As such, suction applied to needle 506 will draw liquid drug from only one of chambers 204. In other embodiments of the invention, side-slit holes 502 and septa 504 may be arranged such that liquid drug may be drawn from two or more or from any combination of chambers 204. In various embodiments, an actuator may be used to move needle 506 back and forth within the fluid path 210.

Figure 6:
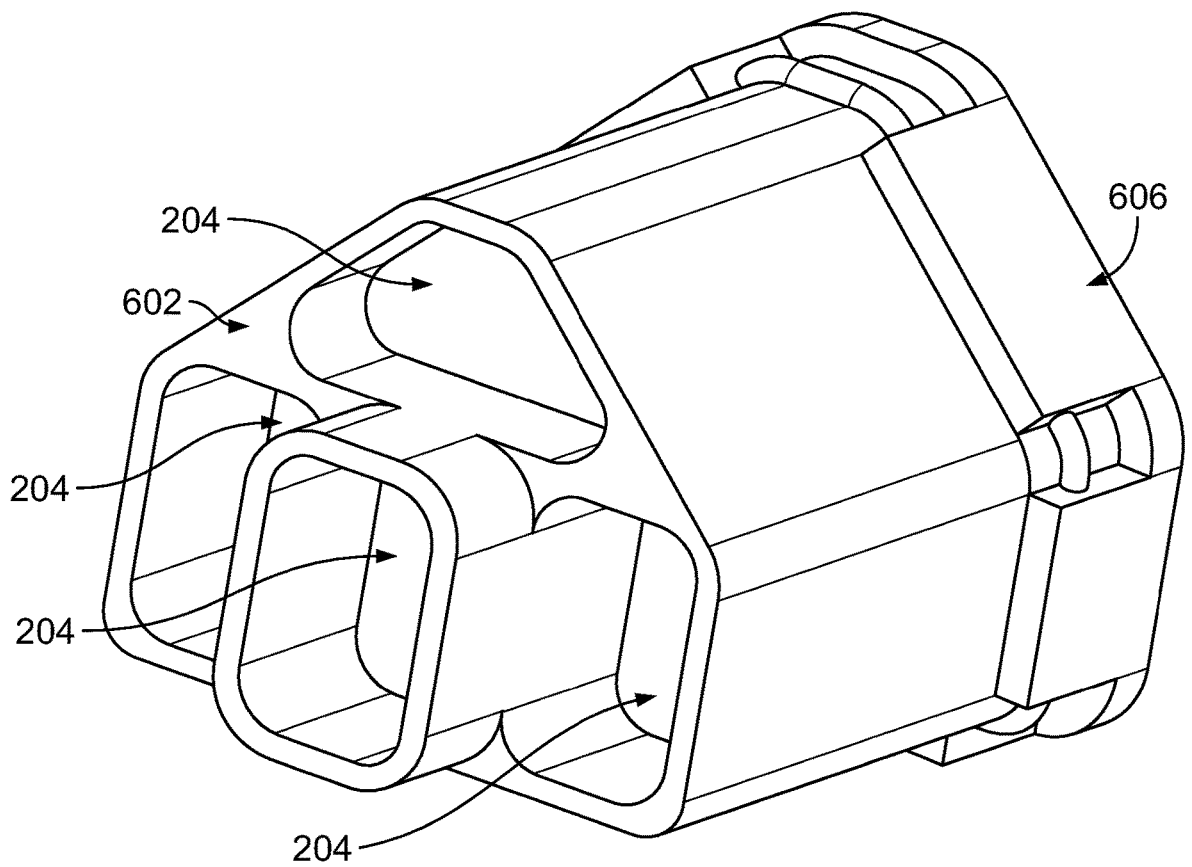
FIG. 6 is a perspective view of a second embodiment of the invention having multiple chambers in the stacked configuration and free pistons.
Figure 7A:
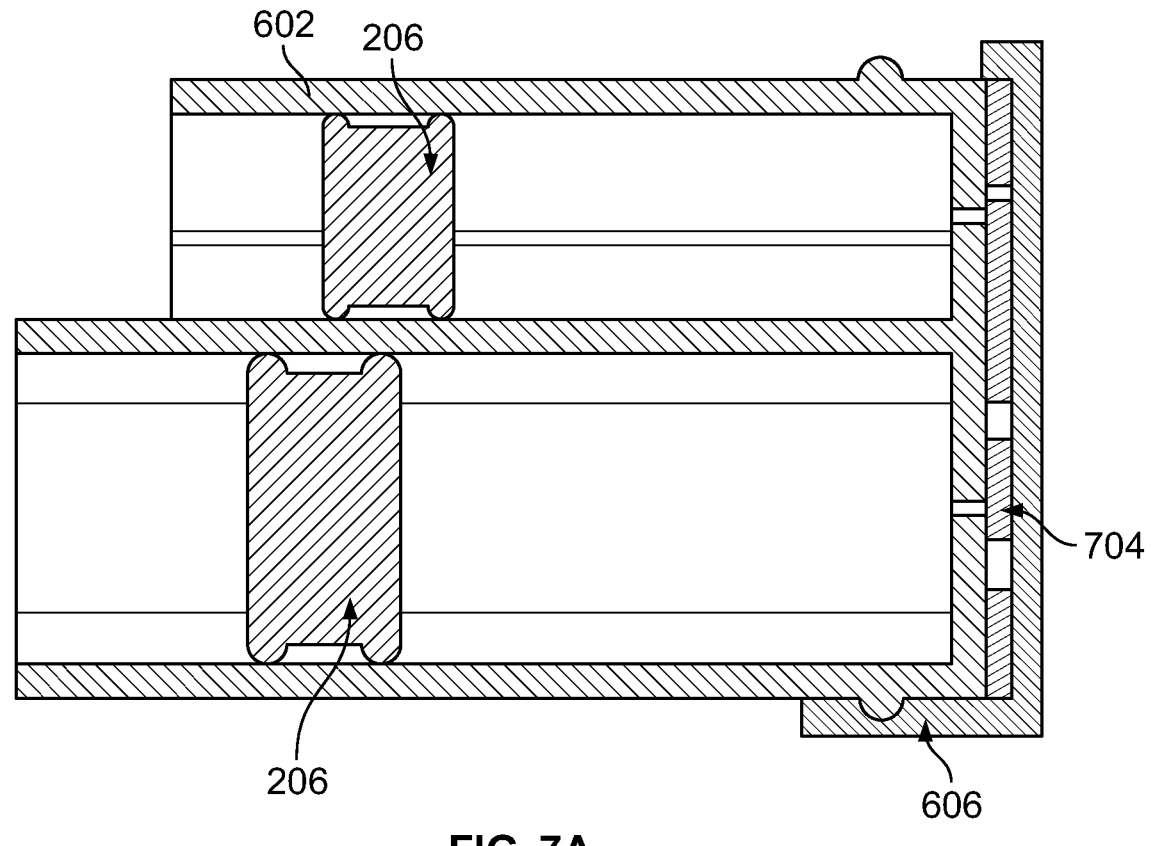
FIG. 7(*a*) is a side cross-sectional view of the second embodiment of FIG. 6.
Figure 7B:
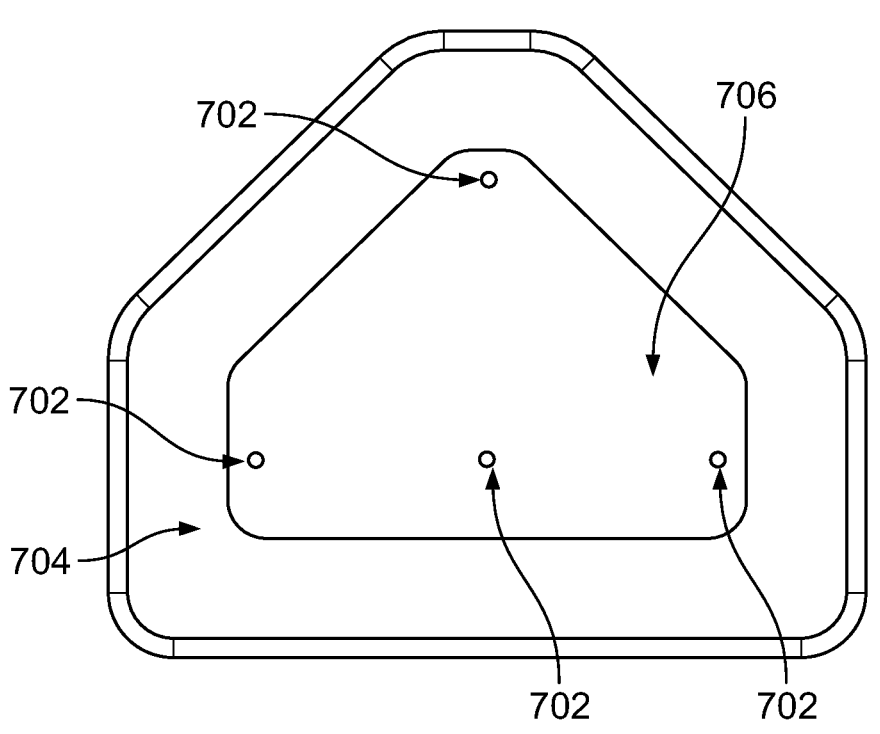

FIGS. 6 and 7(a,b) show yet another embodiment of the invention in which chambers 204 are provided in a stacked configuration. With respect to this embodiment, it should be noted that the chambers need not be of the same size or shape, but may be of any convenient size or shape to best fit the reservoir within the housing of wearable drug delivery device 100. As with previous embodiments, the chambers 204 may be molded into a single unitary body 602 or may be molded individually and joined together. In this embodiment, because the chambers are not aligned, the fluid path cannot be implemented as a single straight void. Instead, as shown in FIG. 7(b), each of chambers 204 may be in fluid communication with a manifold 706 via fluid connections 702. Manifold 706 may be sealed around its edges via sealing gasket 704 and may be further defined by end cap 606 shown in cross-sectional view in FIG. 7(a) and in perspective view in FIG. 6. End cap 606 may be affixed to body 602 of the reservoir via a snap fit, an adhesive, a plastic weld, or via any other means. End cap 606 may be further configured with a fill/dispense port (not shown) for moving the liquid drug to or from manifold 706. Applying suction to the fill/dispense port may create a suction within manifold 706 thereby drawing liquid drug from chambers 204 via connections 702 into manifold 706 and ultimately out through the fill/dispense port defined in end cap 606.

Figure 8A:
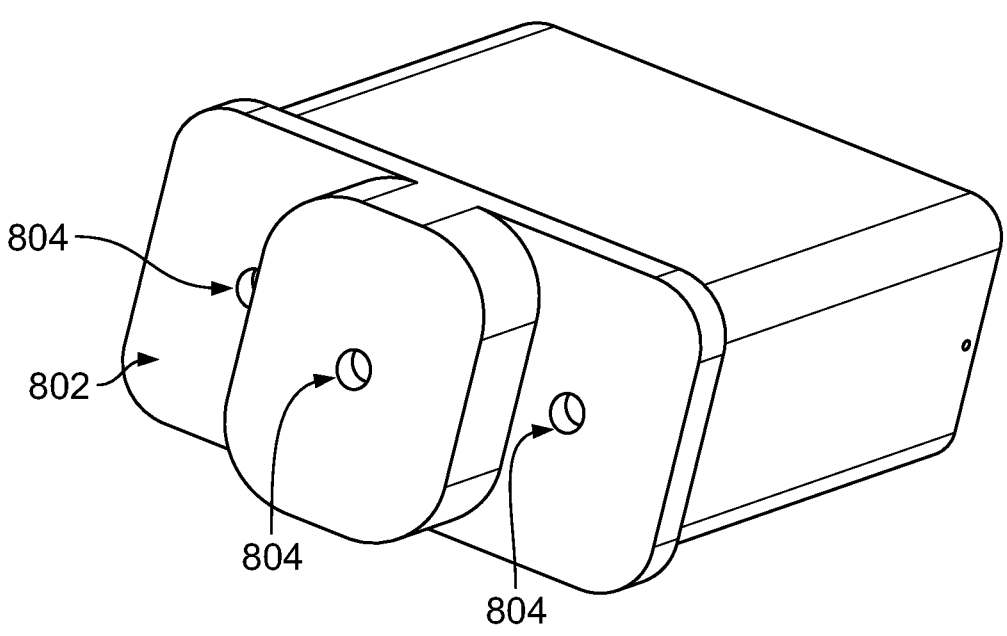
FIG. 8(*a, b*) are perspective views of first and second embodiments of the invention, respectively, showing and cap configurations.
Figure 8B:
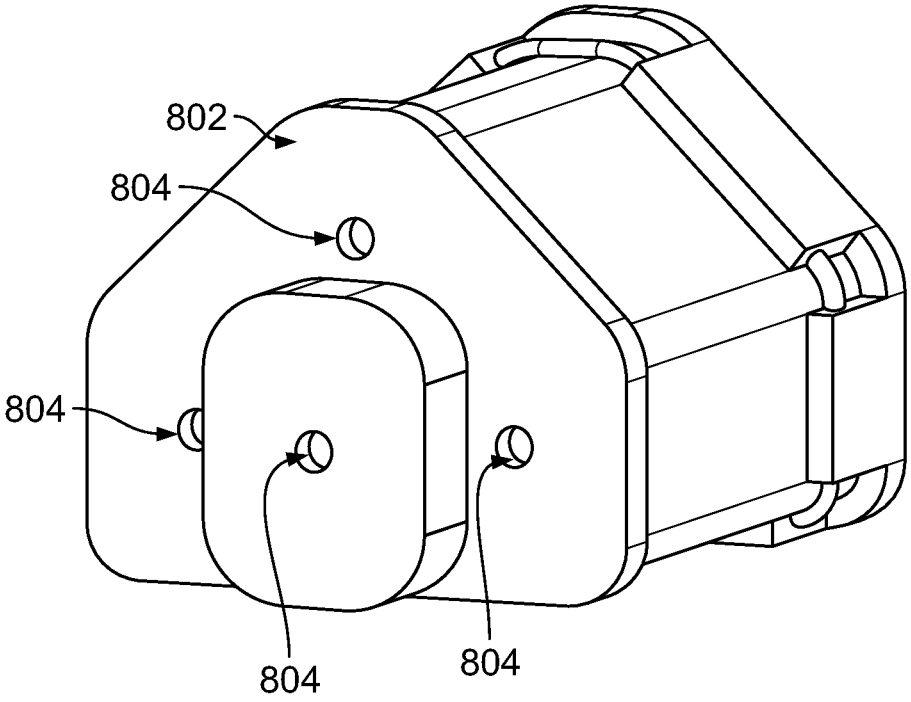

In one variation of embodiments shown in FIG. 2 and FIG. 6, the open end of chambers 204 may be fitted with a cap 802, shown in FIG. 8, to prevent pistons 206 from being pushed from the open ends of chambers 204 as a result of overfilling of chambers 204. This is especially important in embodiments where chambers have differing lengths such that shorter chambers will become full before longer chambers but will still be subjected to the liquid drug under pressure until the longer chambers also become full. Cap 802 may be provided with a venting hole 804 for each of chambers 204 to provide for pressure equalization as each piston 206 is forced toward the open end of its respective chamber 204.

Figure 9:
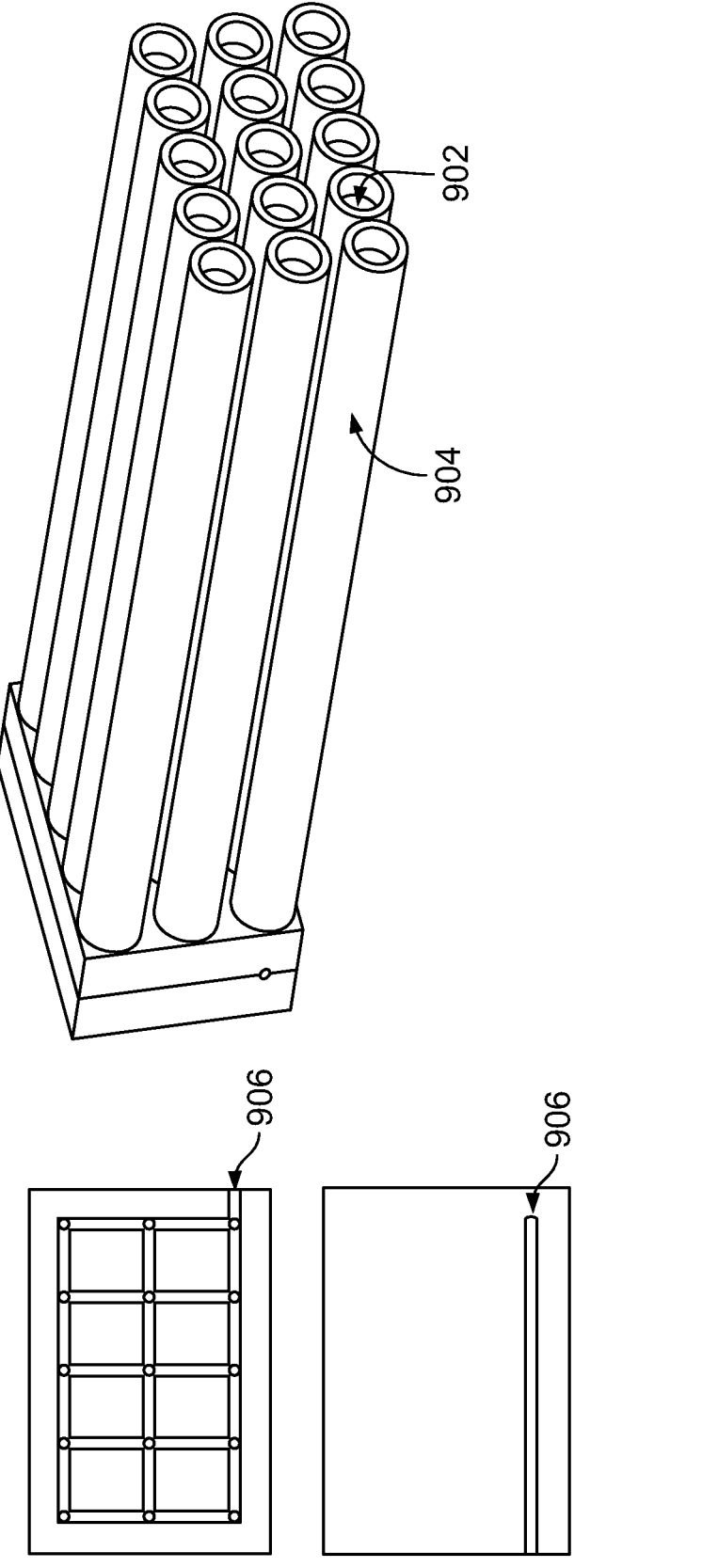
FIG. 9 is a perspective view of the third embodiment of the invention showing multiple tube-shaped chambers comprising the reservoir.

FIG. 9 shows another variation of the embodiments of FIG. 2 and FIG. 6 in which an array of chambers 904 is used. Each of chambers 904 may comprise a thin-walled tube and may be fitted with a spherical piston 902. In this embodiment, the fluid path may comprise a two-part injection molded structure having intersecting fluid paths 910 from each of chambers 904, thereby allowing the liquid drug to be drawn from chambers 904 into the intersecting fluid paths 910 by suction applied to fill/dispense port 908 which is in fluid communication with the intersecting fluid paths 910. Although FIG. 9 shows an embodiment having chambers of equal length, it should be realized that this variation of the reservoir may be implemented with any number of chambers 904 arranged in any configuration and having individual chambers 904 of any given length. As can be seen, this embodiment of the invention provides ultimate control over the use of the space within the housing of wearable drug delivery device 100 as the overall shape of the reservoir may be configured to utilize as much of the unused space within the housing as possible and may also be configured to accommodate other components within the housing of the wearable drug delivery device 100.

The following examples pertain to further embodiments:

Example 1 is a reservoir having a plurality of chambers wherein each chamber has an open end and a free piston disposed therein, a fluid path wherein each of the chambers is in fluid communication with the fluid path, and a fill/dispense port in fluid communication with the fluid path.

Example 2 is an extension of Example 1, or any other example disclosed herein, wherein forcing fluid under pressure into the fill/dispense port causes the plurality chambers to fill with the fluid and the free pistons in each of the chambers to move toward the open end of the chamber.

Example 3 is an extension of Example 1, or any other example disclosed herein, wherein applying suction or a vacuum to the fill/dispense port causes the fluid to be drawn from one or more the chambers into the fluid path and further causes the pistons within each chamber to move away from the end cap (or previously open end) of the chamber.

Example 4 is an extension of Example 1, or any other example disclosed herein, wherein the fluid connection for each chamber is aligned along a line, resulting in a fluid path being a straight void.

Example 5 is an extension of Example 4, or any other example disclosed herein, wherein the reservoir further comprises a cannula ball disposed in the fluid path and having a higher resistive force with respect to the fluid path than the pistons do with the chambers to prevent the cannula ball from moving when suction is applied at the fill/dispense port to move fluid from the chambers.

Example 6 is an extension of Example 5, or any other example disclosed herein, wherein the cannula ball is drawn by suction toward the fill/dispense port when all of the chambers are empty.

Example 7 is an extension of Example 5, or any other example disclosed herein, further comprising a venting port which allows air into the fluid path to allow movement of the cannula ball within the fluid path.

Example 8 is an extension of Example 4, or any other example disclosed herein, further comprising a needle in the fluid path having a plurality of slit holes defined therein and a plurality of septa disposed in a fluid path, such that movement of the needle back and forth in the fluid path will cause one or more of the side-slit holes in the needle to be aligned with one or more the chambers and all other side-slit holes to be blocked by one or more of the septa.

Example 9 is an extension of Example 8, or any other example disclosed herein, further comprising an actuator for moving the needle back and forth within the fluid chamber.

Example 10 is an extension of Example 1, or any other example disclosed herein, wherein the chambers may be of differing lengths.

Example 11 is an extension of Example 1, or any other example disclosed herein, wherein the fluid path comprises a manifold.

Example 12 is an extension of Example 1, or any other example disclosed herein, wherein the fluid path comprises a plurality of intersecting fluid paths.

Example 13 is an extension of Example 2, or any other example disclosed herein, further comprising a cap covering the open ends of the plurality of chambers to prevent the pistons from being forced out of the open ends of the chambers as the chambers are filled with fluid.

Example 14 is an extension of Example 13, or any other example disclosed herein, further comprising one or more venting holes defined in the cap to allow movement of the pistons toward the open ends of the chambers.

Example 15 is an extension of Example 12, or any other example disclosed herein, wherein the plurality of chambers are an array of thin-walled tubing and wherein each piston is a spherical piston.

Example 16 is an extension of Example 1, or any other example disclosed herein, wherein the reservoir is disposed within the housing of a wearable drug delivery device.

Example 17 is an extension of Example 16, or any other example disclosed herein, wherein the chambers are varied in length and arrangement to efficiently utilize available space in the housing of the wearable drug delivery device.

Certain embodiments of the present invention were described above. It is, however, expressly noted that the present invention is not limited to those embodiments, but rather it is intended that additions and modifications to the expressly described embodiments herein are also to be included within the scope of the invention. Moreover, it is to be understood that the features of the various embodiments described herein are not mutually exclusive and can exist in various combinations and permutations, even if such combinations or permutations were not made express herein, without departing from the spirit and scope of the invention. As such, the invention is not to be defined only by the preceding illustrative description. Future filed applications claiming priority to this application may claim the disclosed subject matter in a different manner and may generally include any set of one or more limitations as variously disclosed or otherwise demonstrated herein.

The invention claimed is:

1. A reservoir comprising:
a plurality of chambers, each chamber having an open end and having a free piston that is driven by a suction or vacuum force disposed therein;
a fluid path, wherein each of the plurality of chambers is in fluid communication with the fluid path via a fluid connection opposite the open end of each chamber; and
a fill/dispense port, in fluid communication with the fluid path.

2. The reservoir of claim 1 wherein forcing a fluid under pressure into the fill/dispense port causes each of the plurality of chambers to fill with the fluid and move the free piston in each of the chambers toward the open end of the chamber.

3. The reservoir of claim 1 wherein applying a suction to the fill/dispense port causes a fluid to be drawn from one or more of the chambers, the suction causing the free piston within each of the one or more chambers to move away from the open end of the chamber.

4. The reservoir of claim 1 wherein the fluid connection for each chamber is aligned along a line and further wherein the fluid path is a straight void.

5. The reservoir of claim 4 further comprising:
a cannula ball disposed within the fluid path, the cannula ball having a higher resistive force with respect to the fluid path than each of free pistons has with respect to its respective chamber.

6. The reservoir of claim 5 wherein the cannula ball is drawn by a suction toward the fill/dispense port when all of the plurality of chambers are empty.

7. The reservoir of claim 5 further comprising:
a venting port allowing air to enter the fluid path such that the cannula ball may be drawn toward the fill/dispense port.

8. The reservoir of claim 4 further comprising:
a needle disposed within the fluid path, the needle having a plurality of side-slit holes defined therein equal to the number of chambers; and
a plurality of septa disposed within the fluid path;
wherein movement of the needle within the fluid path in either direction causes one or more of the side-slit holes in the needle to be aligned with one or more of the chambers and further wherein all other side-slit holes defined in the needle are blocked by one of the plurality of septa, such that a fluid may be drawn from one or more chambers of the plurality of chambers without drawing the fluid from the others of the plurality of chambers.

9. The reservoir of claim 8, further comprising:
an actuator for moving the needle in either direction within the fluid path.

10. The reservoir of claim 1 wherein at least one of the plurality of chambers has a different length than at least one other of the plurality of chambers.

11. The reservoir of claim 1 wherein the fluid path comprises a manifold in fluid communication with each of the plurality of chambers and with the fill/dispense port.

12. The reservoir of claim 1 wherein the fluid path comprises a plurality of intersecting fluid paths in fluid communication with each of the plurality of chambers and with the fill/dispense port.

13. The reservoir of claim 2 further comprising:
a cap covering the open end of each of the plurality of chambers, the cap preventing the free piston disposed within each respective chamber from being pushed out of the chamber by a force of a pressurized fluid entering the chamber from the fluid path.

14. The reservoir of claim 13 further comprising:
one or more venting holes defined in the cap allowing movement of the free piston disposed within each chamber toward the open end of its respective chamber.

15. The reservoir of claim 12 wherein the plurality of chambers comprises an array of tubes and wherein each piston is a spherical piston.

16. The reservoir of claim 1 wherein the reservoir is disposed within a housing of a wearable drug delivery device.

17. The reservoir of claim 16 wherein the plurality of chambers are varied in length or arrangement so as to efficiently utilize available space within the housing of the wearable drug delivery device.

* * * * *